(12) United States Patent
Xu

(10) Patent No.: US 11,253,387 B2
(45) Date of Patent: Feb. 22, 2022

(54) ANATOMICAL RING WITH DISCRETE THUMPING ELEMENT

(71) Applicant: California Exotic Novelties LLC, Ontario, CA (US)

(72) Inventor: Chang Gen Xu, Shenzhen (CN)

(73) Assignee: California Exotic Novelties LLC, Ontario, CA (US)

( * ) Notice: Subject to any disclaimer, the term of this patent is extended or adjusted under 35 U.S.C. 154(b) by 3 days.

(21) Appl. No.: 16/854,763

(22) Filed: Apr. 21, 2020

(65) Prior Publication Data

US 2021/0322202 A1 Oct. 21, 2021

(51) Int. Cl.
*A61H 19/00* (2006.01)
*A61F 5/41* (2006.01)

(52) U.S. Cl.
CPC .......... *A61F 5/41* (2013.01); *A61F 2005/414* (2013.01); *A61F 2005/418* (2013.01)

(58) Field of Classification Search
CPC ...... A61F 5/41; A61F 5/451; A61F 2005/411; A61F 2005/414; A61F 2005/417; A61H 19/00; A61H 19/30; A61H 19/32; A61H 19/34; A61H 19/50; A61H 2201/165; A61H 2201/1652
See application file for complete search history.

(56) References Cited

U.S. PATENT DOCUMENTS

| 9,265,688 B2 | 2/2016 | Shim | |
| 2003/0181835 A1* | 9/2003 | Klein | A61H 19/32 |
| | | | 601/72 |
| 2006/0178602 A1* | 8/2006 | Teng | A61H 19/34 |
| | | | 601/70 |
| 2008/0027361 A1* | 1/2008 | Lin | A61H 23/0254 |
| | | | 601/46 |
| 2009/0105529 A1* | 4/2009 | Crarer | A61H 19/32 |
| | | | 600/38 |

OTHER PUBLICATIONS

EBAY, 10_Grades_Rechargeable_Vibrating_Cockring_Massager_For_Men_Couple_Sex_Toy_Luvkis_1, <https://www.ebay.com/itm/10-Vibrating-Cock-Ring-Vibration-Penis-Enhancer-Prolong-Sex-toys-for-Men-Couple/184564006059?hash=item2af8df3cab:g:yRAAAOSw~xRgM3Sj&var=692279109388>, at least as early as Jul. 2019, 6 pages.
VIBEHOUSE, Tammy Double Ring Couple's Vibrator, <http://www.vibe-house.com/shop/tammy/>, at least as early as Mar. 2019, 24 pages.
CALEXOTICS,Naughty Bits Horny AF Vibrating Cock Ring , <https://calexotics.com/naughty-bits-horny-af-vibrating-cock-ring-0-57-3-gold.html>, at least as early as Apr. 2019, 5 pages.

* cited by examiner

*Primary Examiner* — Samuel G Gilbert

(57) ABSTRACT

An anatomical ring device for attachment to a penis includes a ring body defining an interior opening that is shaped and sized to receive a penis. A stimulation unit is disposed on one side of the ring body. A discrete stimulation element is movably disposed on the stimulation unit. A motor is disposed within the stimulation unit. The motor is operably connected to the discrete stimulation element to cause independent movement thereof relative to the stimulation unit.

16 Claims, 3 Drawing Sheets

ANATOMICAL RING WITH DISCRETE THUMPING ELEMENT

BACKGROUND

1. Field

The present disclosure relates to anatomical devices that enhance sexual performance and/or treat impotence in human males. More particularly, the disclosure concerns an anatomical ring device for attachment to the base of a human penis.

2. Description of the Prior Art

By way of background, anatomical rings have been developed for enhancing male sexual performance and/or treating conditions such as erectile dysfunction. Such devices are sometimes colloquially referred to as penis rings. Penis rings are of generally circular configuration and designed to slide onto a penis until its base is reached, usually when the penis is already fully or partially erect. In some applications, the ring is situated in front of the scrotum. In other applications, the ring is situated behind the scrotum. The ring is sized to apply a compressive force that constricts the penis. Much like a valve, this constriction prevents the blood that engorges the erectile tissue from flowing away from the penis. In this way, a penis ring can increase the strength of the erection and/or help sustain it for a longer period of time than would otherwise be possible.

Insofar as penis rings are often worn during sexual intercourse, ring designers have directed attention to enhancing ring functionality so as to provide stimulation to the wearer's partner. For example, modified penis rings have been developed that include a housing containing a battery-powered vibrator. The vibrator housing typically extends from one side of the ring, and the ring is worn so that the housing sits atop the penis. In this position, the housing is able to contact the female clitoral region and deliver vibratory stimulation thereto at the point of maximum penile thrust penetration.

The vibrator mechanisms within the housings of such penis rings invariably incorporate the usual sex toy design wherein a vibrator motor mounts an eccentric weight on its output shaft. As the motor rotates the shaft, the weight swings around the shaft axis so as to generate off-axis forces. The off-axis forces set up vibrations that emanate into the structure of the surrounding vibrator housing. The housing vibrations are usually quite diffuse, and may be be felt by touching virtually any portion of the housing.

Applicant submits that it would be desirable to provide an anatomical ring that is capable of delivering more effective stimulation to the ring wearer's partner than is possible with conventional vibrator technology. Applicant proposes in particular a novel design for an anatomical ring that can deliver intense and targeted stimulation to a partner's clitoral region.

SUMMARY

An anatomical ring device for attachment to a penis includes a ring body defining an interior opening that is shaped and sized to receive a penis. A stimulation unit is disposed on one side of the ring body. A discrete stimulation element is movably disposed on the stimulation unit. A motor is disposed within the stimulation unit. The motor is operably connected to the discrete stimulation element to cause independent movement thereof relative to the stimulation unit.

In an embodiment, the discrete stimulation element may be disposed at an opening in the stimulation unit.

In an embodiment, the discrete stimulation element may cover a raised opening in the stimulation unit.

In an embodiment, the discrete stimulation element may comprise a flexible member covering a raised opening in the stimulation unit.

In an embodiment, the flexible member may be part of an elastomeric sheath that covers a stimulation unit housing in which the raised stimulation unit opening is formed.

In an embodiment, the opening in the stimulation unit may be circular and the flexible member may be button-shaped.

In an embodiment, the discrete stimulation element may be driven by the motor for movement along an axis that forms an acute angle with a central axis of the ring body interior opening.

In an embodiment, the discrete stimulation element may be driven by the motor to provide a thumping action.

In an embodiment, the motor may be operably connected to the discrete stimulation element by a linkage mechanism.

In an embodiment, the linkage mechanism may include a reciprocating piston that reciprocates the stimulation element.

In an embodiment, the reciprocating piston may be attached to the discrete stimulation element.

In an embodiment, the reciprocating piston may be attached to the discrete stimulation element by way of a ball-and-socket connection.

In an embodiment, the linkage mechanism may include a rocker shaft that drives the reciprocating piston via a crank.

In an embodiment, the linkage mechanism may include a slotted drive lever that pivots in order to rock the rocker shaft.

In an embodiment, the linkage mechanism may include a drive wheel having a pin that engages a slot in the slotted drive lever to pivot the lever.

In an embodiment, the motor may comprise an electric motor powered by a battery in the stimulation unit.

In an embodiment, the motor may comprise a rotating output shaft that is operably connected to rotate the drive wheel.

In an embodiment, the output shaft may be operably connected to the drive wheel via a gear system.

In an embodiment, the gear system may be a speed-reduction gear system.

In an embodiment, the motor may deliver pulsatile reciprocating power to the discrete stimulation element by way of the gear system and linkage mechanism.

In another aspect, an anatomical ring device for attachment to a penis includes a ring body defining an interior opening that is shaped and sized to receive a penis. A stimulation unit is disposed on one side of the ring body. A discrete stimulation element is movably disposed on the stimulation unit. A motor is disposed within the stimulation unit. The motor is operably connected to the stimulation element via a linkage mechanism to cause independent reciprocating movement of the discrete stimulation element relative to the stimulation unit.

In another aspect, an anatomical ring device for attachment to a penis includes a ring body defining an interior opening that is shaped and sized to receive a penis. A stimulation unit is disposed on one side of the ring body. A discrete stimulation element is movably disposed on the stimulation unit. A motor is disposed within the stimulation unit. The motor is operably connected to the stimulation element via a linkage mechanism to cause independent movement of the thereof relative to the discrete stimulation unit in the form of a thumping action.

BRIEF DESCRIPTION OF THE DRAWINGS

The foregoing and other features and advantages will be apparent from the following more particular description of example embodiments, as illustrated in the accompanying Drawings.

DETAILED DESCRIPTION OF EXAMPLE EMBODIMENTS

Figure 1:
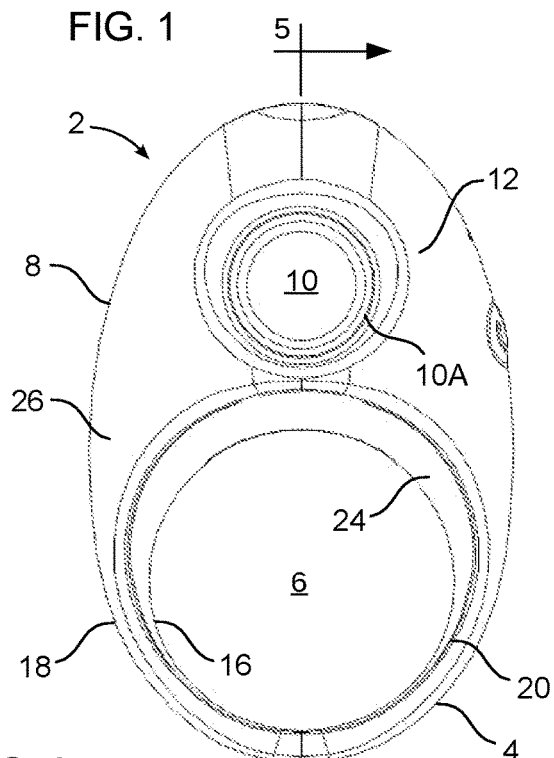
FIG. 1 is front plan view of an anatomical ring device constructed in accordance with an embodiment of the present disclosure.

Turning now to the figures, wherein like reference numerals represent like elements in all of the several views, FIGS. 1-4 depict an anatomical ring device 2 for attachment to a human penis (not shown). In the illustrated embodiment, the ring device 2 includes a ring body 4 that defines an interior opening 6 that is shaped and sized to receive the penis of a wearer of the device. Situated on one side of the ring body 4 is a stimulation unit 8 having a discrete stimulation element 10 movably disposed thereon for delivering targeted stimulation to the wearer's partner during sexual intercourse. As shown in FIG. 1, the stimulation element 10 may be configured as a circular button-shaped member. Movable members of other shapes and sizes may also be used to implement the stimulation element 10.

As described more detail below, a motor disposed within the stimulation unit is operably connected to the stimulation element 10 in a manner that produces independent and isolated movement thereof relative to the stimulation unit 8 as a whole. In an embodiment, the independent movement of the stimulation element 10 is a thumping action in which the stimulation element reciprocates in and out (frontward and rearward) with respect to a front face 12 of the stimulation unit 8. The direction of the stimulation element's reciprocating movement is shown by the double-headed arrow 14 in FIGS. 3 and 4. During use of the device 2, the stimulation element 10 is reciprocally driven to produce its targeted thumping action while the remainder of the stimulation unit 8 is not reciprocally driven and remains stationary (apart from ancillary vibrations that may emanate from the motor and other moving components therein).

Figure 3:
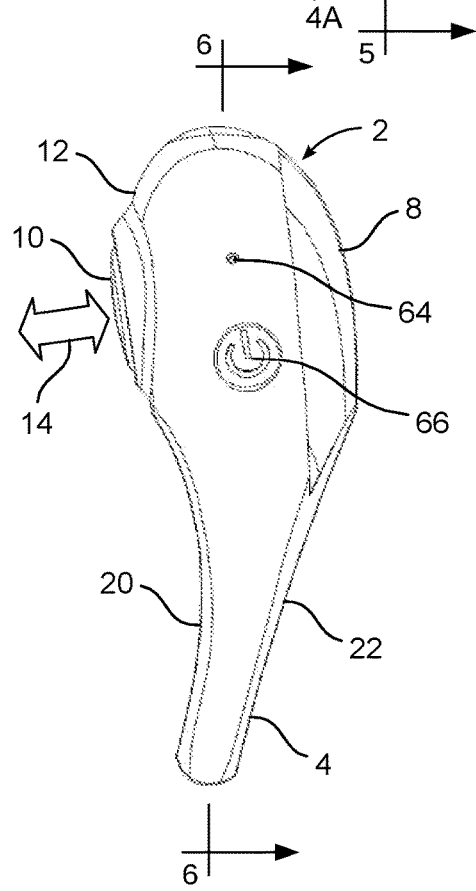
FIG. 3 is a side view showing a first side of the anatomical ring device of FIG. 1.
Figure 4:
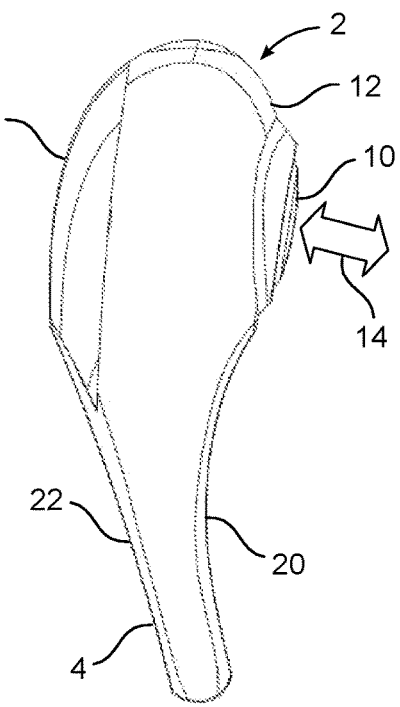
FIG. 4 is a side view showing a second side of the anatomical ring device of FIG. 1.

The ring body 4 may be formed as a closed uninterrupted hoop or band. Although not shown, the ring body 4 could be alternatively formed as an open hoop or band having a gap that allows for expansion and flexing (e.g., at the ring location 4A in FIGS. 1 and 2). The interior opening 6 of the ring body 4 is shaped and sized to receive the wearer's penis. The interior opening 6 may be defined by a generally circular inner edge surface 16 that may engage the base of the penis during use. A generally circular outer edge surface 18 may be spaced laterally (radially) outwardly from the inner edge surface 16. As best shown in FIGS. 3 and 4, the ring body 4 may further include first and second face surfaces, namely, a front face surface 20 that may face away from the user's torso during use and a rear face surface 22 that is axially spaced from the front face surface and may face toward the user's torso during use.

Figure 2:
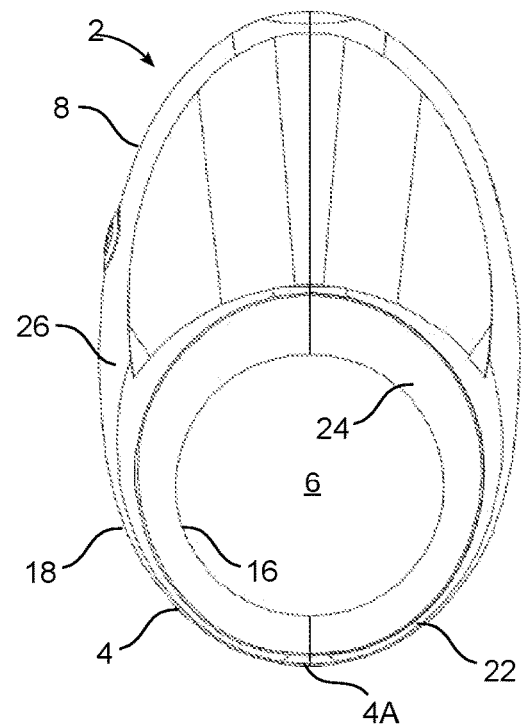
FIG. 2 is a rear plan view of the anatomical ring device of FIG. 1.

It will be appreciated that although the interior opening 6 is shown to be generally circular in FIGS. 1 and 2, other embodiments (not shown) may utilize different ring body shapes and configurations. For example, instead of the interior opening 6 being generally circular, it could be generally oblong (e.g., an oval), generally polygonal (e.g., shaped as a regular or irregular polygon of three sides or more), or implemented with any other shape that is compatible with the cross-sectional configuration of a typical human penis.

The ring body 4 can be made from a suitable elastomeric material, such as a rubber of the type normally used in the manufacture of elastomeric penis rings. By way of example, silicone rubber (polysiloxane) having a durometer hardness of shore 10A-30A may be used. In an embodiment, an inner portion of the ring body 4 that defines the inner edge surface 16 may be separate from the remainder of the ring body, including an outer portion that defines the outer edge surface 18. In particular, the inner portion of the ring body 4 that defines the inner edge surface 16 may be a separate ring insert member 24.

Figure 5:
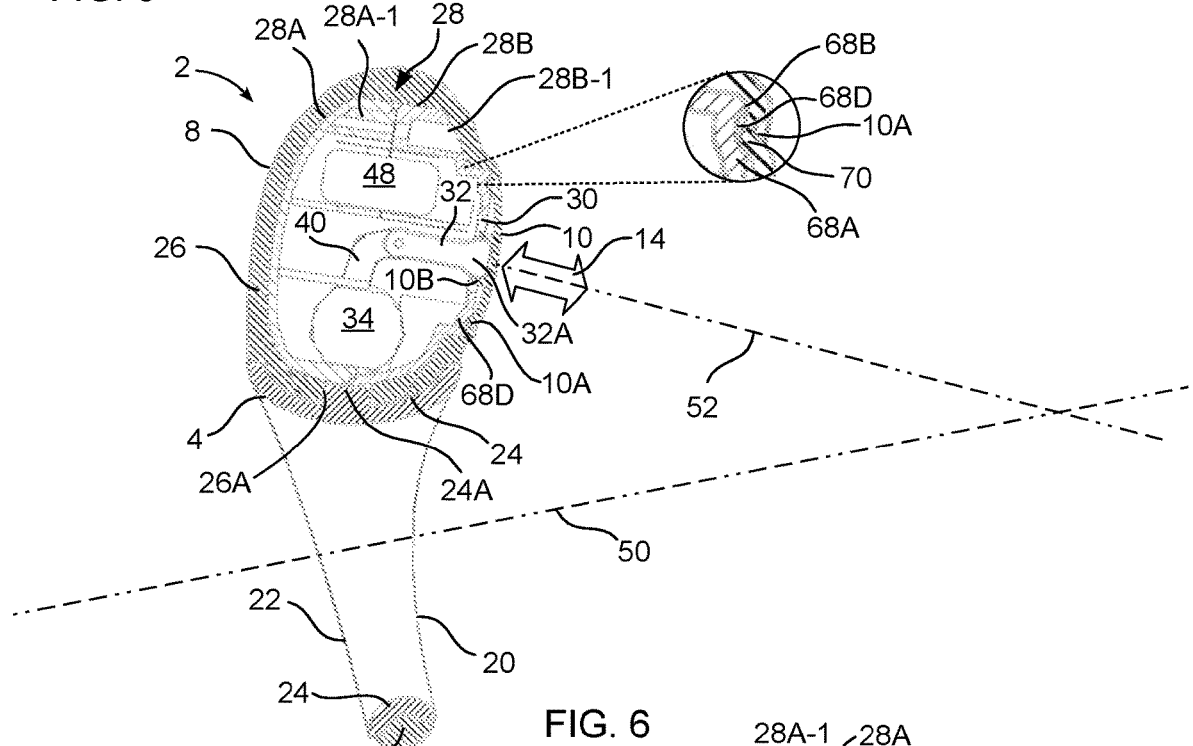
FIG. 5 is a cross-sectional view taken along line 5-5 in FIG. 1.
Figure 6:
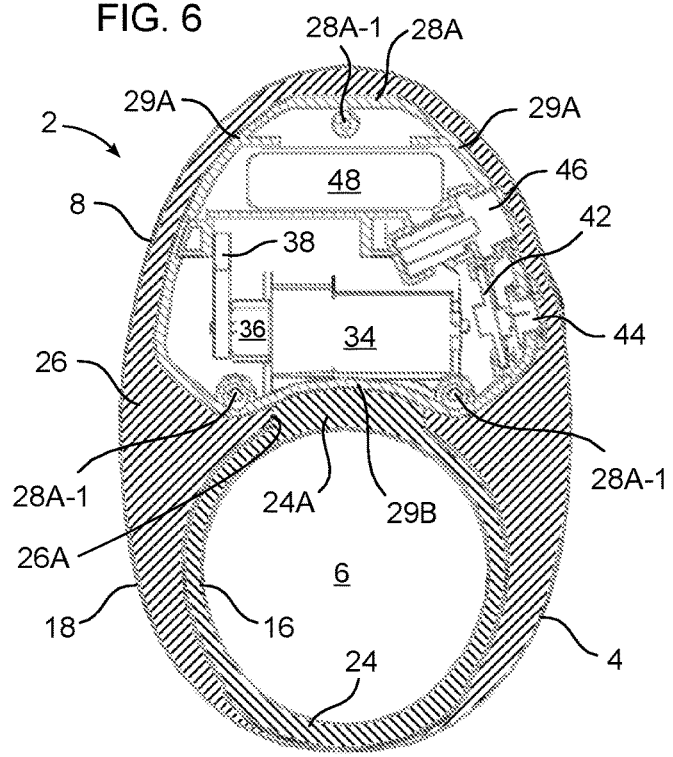
FIG. 6 is a cross-sectional view taken along line 6-6 in FIG. 3.

As shown in FIGS. 5 and 6, the remainder of the ring body 4 that is separate from the ring insert member 24 may be part of a unitary (or substantially unitary) elastomeric sheath 26 that not only forms the outer portion of the ring body, but also extends laterally therefrom, as an appendage of sorts, to define the outer surface of the stimulation unit 8. This extended portion of the elastomeric sheath 26 encapsulates a self-contained stimulation unit housing 28 that is laterally offset from the ring body 4. As described in more detail below, the stimulation unit housing 28 houses the components responsible for actuating the stimulation element 10. It may be fabricated in two sections, namely, a housing rear base member 28A and a housing front cover member 28B.

Each section 28A and 28B of the stimulation unit housing 28 can be made of a suitable rigid plastic material, such as polypropylene, acrylonitrile butadiene styrene (ABS), polyvinyl chloride, high-density polyethylene, etc. Non-plastic materials, such as metals, fiber-reinforced composites, etc., could also be used. The two housing sections 28A and 28B may be joined together in any suitable manner, including by way of fasteners, adhesive, etc. FIGS. 5 and 6 illustrate an embodiment that contemplates the use of fasteners, as can seen by the presence of fastener-receiving holes 28A-1 in the housing rear base member 28A and mating counterbore holes 28B-1 in the housing front cover member 28B.

As shown in FIG. 6, the stimulation unit housing 28 may be generally heart-shaped when viewed from the front or rear of the device 2, with two principal convex sides 29A and one principal concave side 29B. This shape allows the stimulation unit housing 28 to be positioned close to the ring body 4, with the concave side 29B being most proximate to the ring body and tracking part of the lateral contour of the inner edge surface 16. The convex sides 29A of the stimulation unit housing 28 extend away from the ring body 4 and define the outer lateral contour of the stimulation unit 8.

As can be seen in FIGS. 5 and 6, one advantage of forming the ring body 4 with a separate ring insert member 24 is to cover an opening 26A in the elastomeric sheath 26 that may be used to insert the stimulation unit housing 28 inside the sheath. The ring insert member 24 may include a plug portion 24A that plugs the opening 26A in order to seal the stimulation unit housing 28 inside the elastomeric sheath 26. Although the opening 26A is smaller than the stimulation unit housing 28, the material used for the elastomeric sheath 26 should be sufficiently stretchable to accommodate the stimulation unit housing during the insertion process. A suitable adhesive may be used to secure the ring insert member 24 in place onto the outer portion of the ring body 4 after the stimulation unit 8 has been inserted.

As can be seen in FIG. 5, the stimulation element 10 may be formed as part of the elastomeric sheath 26. To provide the flexibility needed for reciprocal movement, the stimulation element 10 may have a thickness that is less than that of the remainder of the elastomeric sheath 26 (e.g., 50% less thick). The circular periphery of the stimulation element 10 may be configured as a living hinge 10A to provide additional flexibility. The living hinge configuration 10A of the stimulation element's periphery may also be seen in FIG. 1. Underneath the stimulation element 10 lies a circular opening 30 in the housing front cover member 28A. The opening 30 allows an internal actuation component within the stimulation unit 8, namely a piston 32, to engage the stimulation element 10 in order to reciprocate it.

The piston 32, along with other actuation components of the stimulation unit 8, are described in more detail below in connection with FIGS. 7 and 8. By way of preview, FIGS. 5 and 6 depict an electric motor 34 and several (but not all) of the components of a linkage mechanism that operably connects the piston 32 to the motor 34. The components of the linkage mechanism shown in FIGS. 5 and 6 include a speed reduction gear system 36, a slotted drive lever 38, and a crank arm 40. Additional components within the stimulation unit that are shown in FIGS. 5 and 6 include a circuit board 42, an on-off/mode-adjustment switch 44, a charge plug receptacle 46, and a battery 48.

In terms of overall configuration, FIGS. 1, 2 and 6 depict an embodiment in which the device 2 is generally oval in shape. The stimulation unit 8 portion of the device 2 may be approximately the same width (in the lateral direction) as the ring body portion of the device. As shown in FIG. 6, the stimulation unit housing 28 may be laterally wider than the interior opening 6 of the ring body 4 in order to provide ample room for the housing's internal components. This configuration results in the lateral thickness of the ring body 4 (i.e., between the inner and outer edge surfaces 16 and 18) being minimal at its most distal point from the stimulation unit housing 28, then gradually increasing in size moving proximally toward the stimulation unit housing. In other embodiments, the stimulation unit housing 28 may be equal in width or even smaller than the interior opening of the ring body 4.

As can be seen from FIGS. 3, 4 and 5, the stimulation unit 8 may be bulbous relative to the ring body 8 in the fore-aft direction of the device 2, which is again due to the stimulation housing 28 being sized to provide ample room for its internal components. As shown in FIG. 5, this configuration results in the fore-aft thickness of the ring body 4 (i.e., between the front and rear faces 20 and 22) being at a minimum at its most distal point from the stimulation unit housing 28, then gradually increasing in size moving proximally toward the stimulation unit housing. In other embodiments, the stimulation unit housing 28 may be equal in fore-aft thickness or even smaller than the interior opening of the ring body 4.

As best shown in FIG. 5, the stimulation unit 8 may be tilted forwardly of the ring body 2, thereby forming an acute angle between a principal axis 50 of the ring body 4 and a reciprocal motion axis 52 of the stimulation element 10. The ring body's principal axis 50 represents the orientation of the wearer's penis when the device 2 is placed thereon. The stimulation element's reciprocal motion axis represents the direction of applied stimulation to the wearer's partner, and is optimized so that the stimulation element 12 will be positioned to deliver intense and targeted stimulation to a partner's clitoral region at the point of maximum penile thrust penetration.

In terms of overall size, the maximum longitudinal length of the device 2 (i.e., along the center of the device in FIGS. 1, 2 and 6) may range between 3.0-4.0 inches, with other lengths also being possible. The maximum lateral width of the device 2 (i.e., at a point between the ring body 4 and the stimulation element 10) may range between 2.0-2.5 inches, with other widths also being possible. The interior opening 6 of the ring body 4 may have a diameter of approximately ranging between 1.5-2.5 inches (which should be suitable for most users), with other diameters also being possible. The radial thickness of the ring body 4, as measured by the lateral spacing between the inner edge surface 16 and the outer edge surface 18, may range between 0.25-0.75 inches, with other radial dimensions also being possible. The axial thickness of the ring body 4, as measured by the axial spacing between the front face surface 20 and the rear face surface 22, may range between 0.25-0.75 inches, with other axial thicknesses also being possible.

With reference now to FIG. 5, the piston 32 within the stimulation unit housing 28 applies direct reciprocating action to the stimulation element 10. In FIG. 5, the stimulation element 10 is in its rearwardly retracted (home) position. During operation of the device 2, the piston 32 repeatedly extends and retracts to produce the stimulation element's thumping motion. During its extension stroke, the piston 32 pushes the stimulation element 10 outwardly from the front of the stimulation unit 8 (i.e., to the right along the reciprocal motion axis 52 in FIG. 5). This causes the stimulation element's elastomeric material to stretch. During its retraction stroke, the piston 32 withdraws away from the stimulation element 10 (i.e., to the left along the reciprocal motion axis 52 in FIG. 5). This relaxes the stretching forces on the stimulation element's elastomeric material, allowing the stimulation element to return to its home position due to its elastomeric shape memory properties.

In an embodiment, a free end of 32A the piston 32 may be attached to the interior side of the stimulation element 10 so that the piston 32 pulls the stimulation element rearwardly during the piston's retraction stroke. The piston's free end 32A may be attached to the interior side of the stimulation element in any suitable manner. In the embodiment of FIG. 5, the free end 32A is formed as (or mounts) a generally ball-shaped member and the interior side of the stimulation element is formed with (or mounts) a socket 10B that encapsulates some or all of the ball-shaped member. This provides a ball-and-socket connection. If needed, adhesive may be applied inside the socket 10B to affix the ball-shaped free end 32A securely in place therein.

Figure 7:
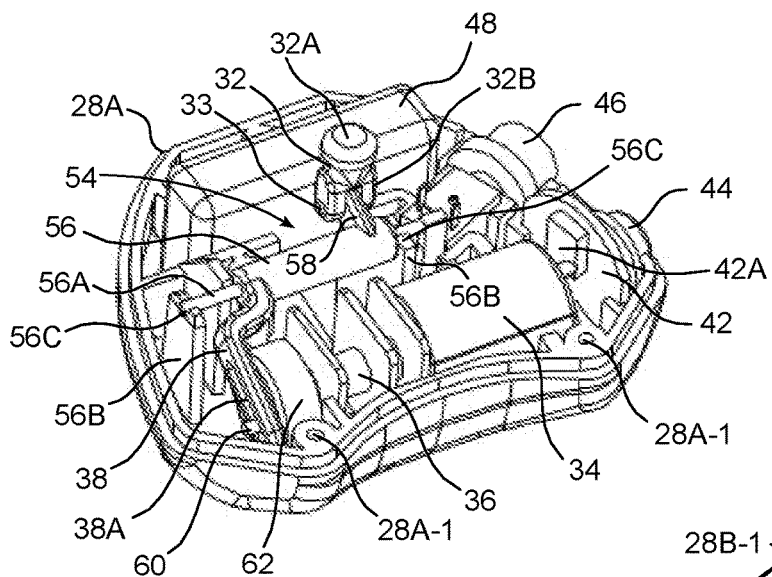
FIG. 7 is a perspective view showing a housing rear base member and internal components of the anatomical ring device of FIG. 1 from a first perspective.
Figure 8:
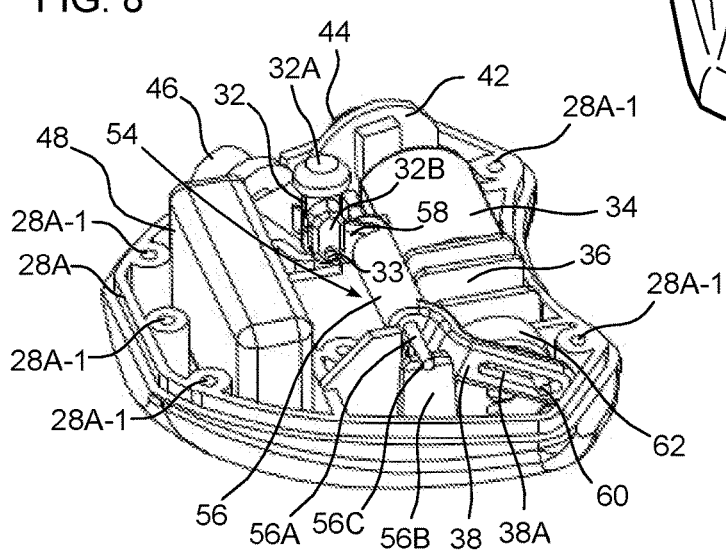
FIG. 8 is a perspective view showing the housing rear base member and internal components of the anatomical ring device of FIG. 1 from a second perspective.

Turning now to FIGS. 7 and 8, further details of the actuation components responsible for reciprocating stimulation element 10 are shown. These components are carried within the rear base member 28A of the stimulation unit housing 28. The piston 32 is part of a linkage mechanism 54 that is actuated by the motor 34 to deliver pulsatile reciprocating power to the stimulation element 10. The linkage mechanism 54 may include a cylindrical rocker shaft 56 that drives the reciprocating piston 32 via a crank 58. The crank 58 may be integrally formed on the rocker shaft 56 or otherwise rigidly affixed thereto, and extends radially outwardly therefrom. A clevis portion 32B of the piston 32 at a base end thereof is pivotally mounted to the crank 58 by way of a pin connection 33. As previously described, the free end 32A of the piston 32 engages the stimulation element 10, and may be attached thereto by way of a ball-and-socket connection (see FIG. 5). The rocker shaft 56 includes an interior rocker pin 56A extending along the rocker shaft's longitudinal axis. The rocker pin 56A is pivotally mounted to a pair of pin support posts 56B on the housing rear base member 28A. The free ends of the pin support posts 56B are notched at 56C to provide a pivot cradle for the rocker pin. Although not shown, the housing front cover member 28B may have a corresponding pair of notched pin support posts. When the two housing segments 28A and 28B are joined together, the opposing notches of the pin support posts on each housing segment will trap the rocker pin 56A and thereby secure the rocker shaft 56 to the stimulation unit housing 28. During operation of the stimulation unit 8, the rocker shaft 56 is driven to rock in alternating back and forth directions. This rocking motion pivots the crank 58 back and forth, which drives the piston 32 through its reciprocating motion as previously stated.

The rocker shaft 56 is induced to rock by the slotted drive lever 38 mentioned above in connection with FIG. 6. The slotted drive lever 38 may integrally formed on the rocker shaft 56 or otherwise rigidly affixed thereto, and extends radially outwardly therefrom. An elongated slot 38A extends longitudinally along the slotted drive lever 38. The slot 38A is engaged by a drive pin 60 that extends from a rotatable drive wheel 62. The drive pin 60 is offset from the axis of rotation of the drive wheel 62, and is parallel thereto. Rotation of the drive wheel 62 thus causes the drive pin 60 to oscillate around the drive wheel's axis of rotation. The drive pin's oscillating motion actuates the slotted drive lever 38, causing it to pivot back in forth in alternating directions. This in turn rocks the rocker shaft 56.

The drive wheel 62 may be indirectly driven by the motor 34 through the speed reduction gear system 36 mentioned above in connection with FIG. 6. In an embodiment, the output shaft of the motor 34, together with the shafts that mount the various gears of the gear system 36, may all be parallel to each other and to the rotational axis of the drive wheel 62. It will be appreciated that the degree of speed reduction provided by the gear system 36 will depend on the speed characteristics of the motor 34 and the desired operating characteristics of the stimulation unit 8. In some cases, the speed reduction gear system 36 may be eliminated if the speed characteristics of the motor 34 are compatible with the stimulation unit's desired operating characteristics.

In the illustrated embodiment, the motor 34 is an electric motor powered by the battery 48, which is preferably rechargeable. The charge port receptacle 46 allows the battery 48 to be recharged from a battery charging device (not shown). The charge port receptacle 46 may be of any suitable type, with the illustrated embodiment depicting a receptacle designed to receive a small-diameter (e.g., 2 mm) coaxial barrel plug connector (see FIG. 6). As shown in FIG. 3, the elastomeric sheath 26 may be formed with a small hole 64 that is situated over the charge port receptacle 46 in order to receive the plug connector.

In the illustrated embodiment, the circuit board 42 mounts a digital controller chip 42A that receives power from the battery 48 and is programmed to deliver control signals to the motor 34 that dictate the operating mode of the stimulation unit 8. In an embodiment, the controller chip 42A may be programmed to produce a number of different operating modes, such as modes that vary the frequency of reciprocation of the stimulation element 10 and/or generate different reciprocation burst patterns (e.g. reciprocation sequences separated by periods of stimulation inactivity). The on-off/mode-adjustment switch 44 may be used for this purpose. By way of example, pressing and holding the switch 44 may activate the stimulation unit 8, pressing the switch 44 one or more times may cycle the stimulation unit through different operating modes, and pressing and holding the switch a second time may deactivate the stimulation unit. As shown in FIG. 3, the elastomeric sheath 26 may be formed with a button emblem 66 that is situated over the switch 44.

Figure 9:
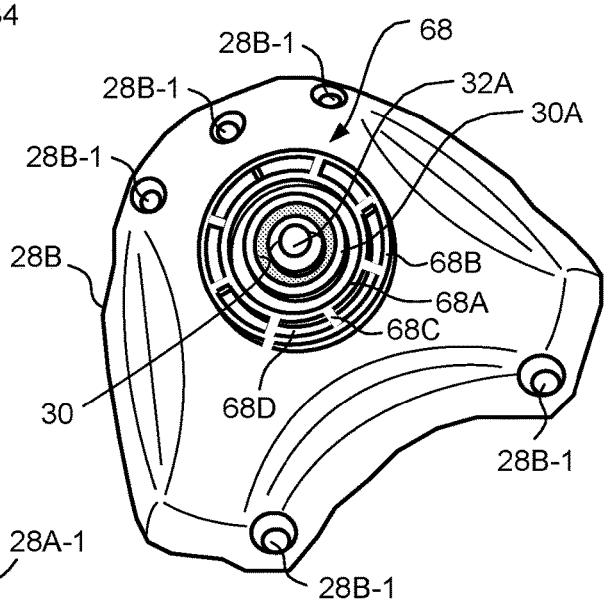
FIG. 9 is a perspective view showing a housing front cover member of the anatomical ring device of FIG. 1.

Turning now to FIG. 9, the front side of the housing front cover member 28B is shown. Situated proximate to the center of this structure is the circular opening 30 through which the piston 32 extends. In an embodiment, the opening 30 may be surrounded by a raised ring flange 30A to form a raised opening that helps guide the piston 32 as it reciprocates. A larger raised double-ring flange 68 may be formed around the exterior of the inside ring flange 30A, and defines additional structure of the raised opening 30. The double-ring flange 68 extends away from the housing front cover member 28B in the frontward direction. It includes an inner ring flange 68A and an outer ring flange 68B, and may further include radial support members 68C extending between the inner and outer ring flanges. An annular space 68D lies between the inner ring flange 68A and the outer ring flange 68B.

The double-ring flange 68 may be sized so that the annular space 68D between the inner ring flange 68A and the outer ring flange 68B lies underneath the living hinge 10A that encircles the stimulation element 10. This is shown in FIG. 5, in which the living hinge 10A is configured as a ring-shaped fold 70 in the elastomeric sheath 26. As best shown in the enlarged inset portion of FIG. 5, the ring-shaped fold of the living hinge 10A extends radially inwardly over the outer ring flange 68B, then deviates rearwardly to seat within the annular space 68D, then extends forwardly and radially inwardly over the inner ring flange 68B to define the outer periphery of the stimulation element 10. In this way, the double-ring flange 68 accommodates flexing of the living hinge 10A.

The double-ring flange 68 also supports and positions the stimulation element 10 at a desired height above the surface of the housing front cover member 28B, so that the entire stimulation element is raised. In an embodiment, the height of the double ring flange 68 may be selected so that the center of the stimulation element 10 is biased slightly forwardly by the piston 32 even when the latter is fully retracted. In this way, the piston 32 will continuously flex the stimulation element and cause it to bulge so that it always maintains a convex forwardly-rounded button shape.

Accordingly, an anatomical ring device for attachment to the base of a human penis has been disclosed. Reference in the present disclosure to "an embodiment" means that a particular feature, structure or characteristic described in connection with the embodiment may be included in at least one embodiment of the disclosed device. Thus, the appearances of the phrase "in an embodiment" in various places throughout the specification are not necessarily all referring to the same embodiment.

For purposes of explanation, specific configurations and details have been set forth herein in order to provide a thorough understanding of the present invention. However, it will be apparent to one of ordinary skill in the art that embodiments of the present invention may be practiced without the specific details presented herein. Furthermore, well-known features may have been omitted or simplified in order not to obscure the present invention. Various examples may be given throughout this description. These examples are merely descriptions of specific embodiments of the invention. The scope of the invention is not limited to the examples given.

As used in this application, the terms such as "front," "frontward," "forward," "rear," "rearward," "upwardly," "downwardly," "inside," "outside," "interior," "exterior," and other orientational descriptors are intended to facilitate the description of the example embodiments of the present disclosure, and are not intended to limit the structure of the example embodiments of the present disclosure to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments. Terms of rough approximation, such as "generally," are understood by those of ordinary skill to refer to a characteristic or feature of that bears resemblance to something, such that it is reasonable to draw a comparison to facilitate understanding, without requiring that the characteristic or feature be exactly the same, or even substantially the same, as the thing to which it is compared.

Although various example embodiments have been shown and described, it should be apparent that many variations and alternative embodiments could be implemented in accordance with the disclosure. It is understood, therefore, that the invention is not to be in any way limited except in accordance with the spirit of the appended claims and their equivalents.

What is claimed is:

1. An anatomical ring device for attachment to a penis, comprising:
    a ring body defining an interior opening that is shaped and sized to receive a penis;
    a stimulation unit on one side of the ring body;
    a discrete stimulation element movably disposed on the stimulation unit;
    a motor disposed within the stimulation unit; and
    the motor being operably connected to the discrete stimulation element to cause independent movement thereof relative to the stimulation unit;
    wherein the discrete stimulation element comprises a flexible member covering a raised opening in the stimulation unit; and
    wherein the flexible member comprises part of an elastomeric sheath that covers a stimulation unit housing in which the raised stimulation unit opening is formed.

2. The device of claim 1, wherein the opening in the stimulation unit housing is circular and the flexible member is button-shaped.

3. The device of claim 1, wherein the discrete stimulation element is driven by the motor for movement along an axis that forms an acute angle with a central axis of the ring body interior opening.

4. The device of claim 1, wherein the discrete stimulation element is driven by the motor to provide a thumping action.

5. The device of claim 1, wherein the motor is operably connected to the discrete stimulation element by a linkage mechanism.

6. The device of claim 5, wherein the linkage mechanism includes a reciprocating piston that reciprocates the discrete stimulation element.

7. The device of claim 6, wherein the reciprocating piston is attached to the discrete stimulation element.

8. The device of claim 7, wherein the reciprocating piston is attached to the discrete stimulation element by way of a ball-and-socket connection.

9. The device of claim 6, wherein the linkage mechanism comprises:
    a rocker shaft that drives the reciprocating piston via a crank;
    a slotted drive lever that pivots in order to rock the rocker shaft; and
    a drive wheel having a pin that engages a slot in the slotted drive lever to pivot the lever.

10. The device of claim 9, wherein the motor comprises an electric motor powered by a battery in the stimulation unit.

11. The device of claim 10, wherein the motor comprises a rotating output shaft that is operably connected to rotate the drive wheel.

12. The device of claim 11, wherein the output shaft is operably connected to the drive wheel via a gear system.

13. The device of claim 12, wherein the gear system is a speed-reduction gear system.

14. The device of claim 13, wherein the motor delivers pulsatile reciprocating power to the discrete stimulation element by way of the gear system and linkage mechanism.

15. An anatomical ring device for attachment to a penis, comprising:
    a ring body defining an interior opening that is shaped and sized to receive a penis;
    a stimulation unit on one side of the ring body;
    a discrete stimulation element movably disposed on the stimulation unit;
    a motor disposed within the stimulation unit;
    the motor being operably connected to the discrete stimulation element to cause independent movement thereof relative to the stimulation unit; and
    wherein the discrete stimulation element is driven by the motor for movement along an axis that forms an acute angle with a central axis of the ring body interior opening.

16. An anatomical ring device for attachment to a penis, comprising:
    a ring body defining an interior opening that is shaped and sized to receive a penis;
    a stimulation unit on one side of the ring body;
    a discrete stimulation element movably disposed on the stimulation unit;
    a motor disposed within the stimulation unit;
    the motor being operably connected to the discrete stimulation element by a linkage mechanism to cause independent movement thereof relative to the stimulation unit; and
    wherein the linkage mechanism includes a reciprocating piston that reciprocates the discrete stimulation element.

* * * * *